United States Patent [19]

Christensen et al.

[11] 4,290,947
[45] Sep. 22, 1981

[54] PROCESS FOR THE PREPARATION OF THIENAMYCIN AND INTERMEDIATES

[75] Inventors: Burton G. Christensen, Scotch Plains; Ronald W. Ratcliffe, Matawan; Thomas N. Salzman, North Plainfield, all of N.J.

[73] Assignee: Merck & Co., Inc., Rahway, N.J.

[21] Appl. No.: 154,190

[22] Filed: May 29, 1980

Related U.S. Application Data

[63] Continuation of Ser. No. 34,052, Apr. 27, 1979, abandoned.

[51] Int. Cl.³ .................. C07D 205/08; C07D 487/04
[52] U.S. Cl. ......................... 260/239 A; 260/245.2 T
[58] Field of Search ..................................... 260/239 A

[56] References Cited

U.S. PATENT DOCUMENTS 4,122,086 10/1978 Hall et al. ........................ 424/270

OTHER PUBLICATIONS

Clauss et al., Chem. Abs. 81, 77753c, (1974).
Huffman et al., Chem. Abs. 88, 183758n, (1978).

Primary Examiner—Mark L. Berch
Attorney, Agent, or Firm—James A. Arno; Hesna J. Pfeiffer

[57] ABSTRACT

Disclosed is a process for the total synthesis of thienamycin from L-aspartic acid via intermediate III:

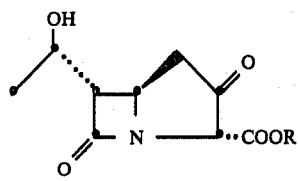

R=H, blocking group or salt cation.

1 Claim, No Drawings

PROCESS FOR THE PREPARATION OF THIENAMYCIN AND INTERMEDIATES

This is a continuation of application Ser. No. 034,052, filed Apr. 27, 1979, now abandoned.

BACKGROUND OF THE INVENTION

This invention relates to the total synthesis of the known antibiotic thienamycin (I).

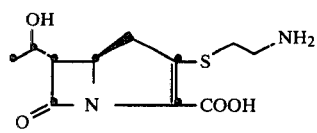

Starting from L-aspartic acid, the synthesis proceeds in a stereo-selective way via intermediates II, III, IV:

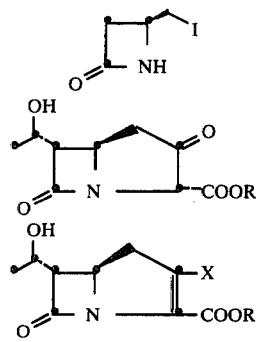

wherein X is a conventional leaving group and R is hydrogen, a conventional, readily removable protecting group or a salt cation. The details of the total synthesis are given below.

DETAILED DESCRIPTION OF THE INVENTION

The process of the present invention may conveniently be summarized by the following reaction diagram:

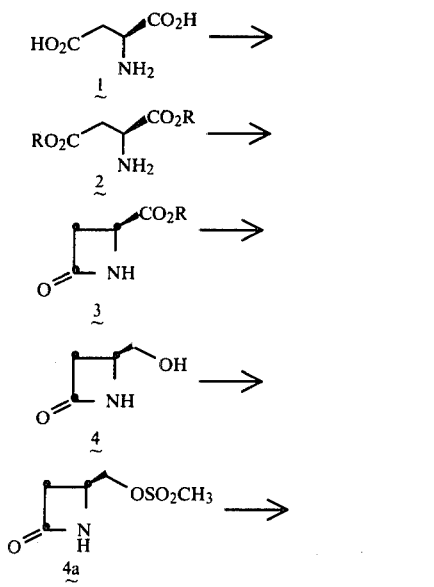

-continued

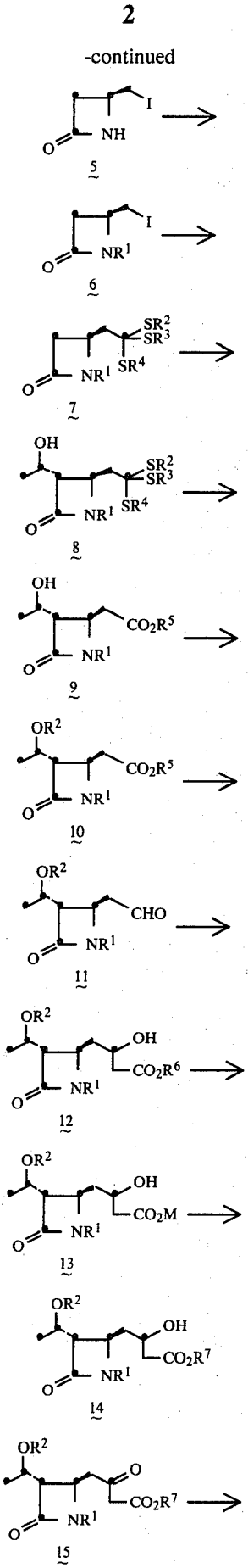

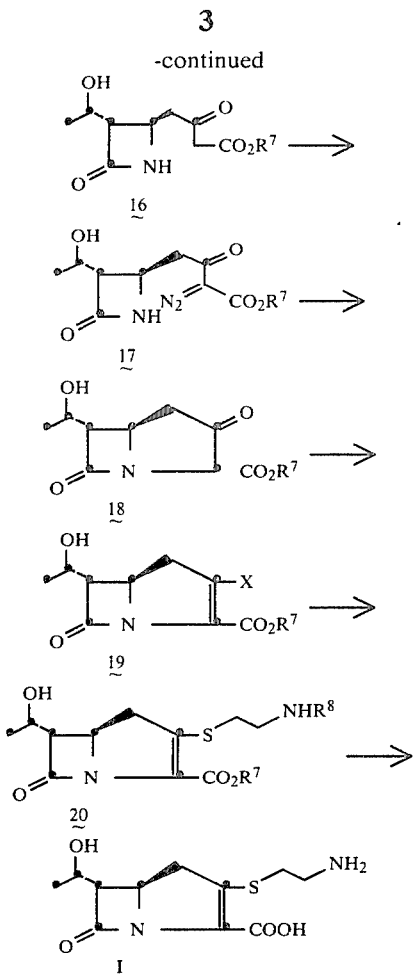

ferred, and typically $R^1$ is established by treating 5 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from $-20°$ to $25°$ C. for from 0.5 to 24 hours in the presence of a base such as triethylamine, diisopropylethylamine, or imidazole.

The transformation 6→7 is accomplished by treating 6 in a solvent such as tetrahydrofuran, dimethoxyethane, diethylether or the like with a carbanion generically represented by the following structure:

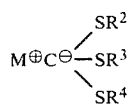

wherein M is a metal cation such as lithium, potassium, copper or magnesium, for example, and $R^2$, $R^3$ and $R^4$ are selected from alkyl, aryl or aralkyl such as methyl, ethyl, benzyl, methoxybenzyl, trityl and phenyl, for example, at a temperature of from $-100°$ to $0°$ C. and from 0.5 to 4 hours.

Typically, the carbanion reagent is prepared prior to addition of substrate 6 on treatment of the triorganothiomethane with a strong base such as n-butyllithium, t-butyllithium, phenyllithium, lithium diisopropylamide(LDA) or the like.

The alkylation 7→8 is accomplished by treating 7 in a solvent such as tetrahydrofuran, dimethoxyethane, diethylether, hexamethylphosphoramide, at a temperature of from $-100°$ to $-20°$ C. with a strong base such as lithium diisopropylamide, lithium hexamethyldisilazide, lithium 2,2,6,6-tetramethylpiperidide, potassium hydride or the like followed by the addition of an equivalent to 10 fold excess of acetaldehyde. This reaction gives a mixture of isomers from which the desired trans-R form can be conveniently separated by chromatography or crystallization.

The transformation 8→9 is accomplished by treating 8 in a solvent such as methanol, ethanol, isopropanol, water or the like at a temperature of from $0°$ to $80°$ C. with a Lewis acid such as mercuric chloride, silver tetrafluoroborate, thallium trinitrate or the like. The value of $R^5$ is determined by the identity of the alcohol taken in reaction.

The transformation 9→10 establishes the hydroxyl protecting group $R^2$. The most preferred protecting groups $R^2$ are triorganosilyl groups such as t-butyldimethylsilyl, t-butyldiphenylsilyl, triphenylsilyl and the like. Typically, silylation is accomplished by treating 9 with the corresponding triorganosilyl chloride in a solvent such as dimethylformamide, acetonitrile, tetrahydrofuran and the like at a temperature of from $-20°$ to $80°$ C. from 0.5 to 24 hours.

The reduction 10→11 is accomplished by treating 10 in a solvent such as toluene, methylene chloride diethylether, tetrahydrofuran and the like with a reducing agent such as diisobutylaluminum hydride, sodium bis(2-methoxyethoxy)aluminum hydride or the like at a temperature of from $-100°$ to $-40°$ C. for from 1 to 10 hours.

The addition 11→12 is accomplished by treating 11 in a solvent such as tetrahydrofuran, diethylether, dimethoxyethane or the like at a temperature of from $-100°$ to $0°$ C. for from 15 minutes to 2 hours in the presence of In words relative to the above diagram, L-aspartic acid 1 is esterified according to well known procedures. Typically 1 in a solvent such as benzene, toluene, chloroform or the like is treated with an esterifying agent such as benzyl alcohol, methanol, ethanol, ispropanol, or the like in the presence of p-toluene sulfonic acid, HCl, HBr, or the like at a temperature of from $0°$ to $110°$ C. for from 1 to 24 hours to achieve the desired establishment and hence protection of the carboxyl functions. The resulting species 2 in a solvent such as ether, THF, DME or the like is treated with trimethylchlorosilane, or the like followed by treatment with EtMgBr, MeMgI, $\phi$MgBr, t-BuMgCl, or the like at a temperature of from "40° to 50° C. for from 1 to 72 hours to provide azetidinone 3. Reduction of species 3 with a reducing agent such as $NaBH_4$, or the like in a solvent such as methanol, ethanol, isopropanol or the like at a temperature of from $-10°$ to $40°$ C. for from 1 to 6 hours provides 4. (For purposes here, the symbols: Et, Me, $\phi$, iPr, and t-Bu stand for: ethyl, methyl, phenyl isopropyl, and tert-butyl, respectively.)

Treatment of 4 in a solvent such as methylene chloride, $CHCl_3$ or the like with methane sulfonyl chloride, methane sulfonic anhydride or the like in the presence of a base such as $Et_3N$, $iPr_2NEt$, or the like followed by treatment with a stoichiometric to 5 fold excess of sodium iodide in acetone yields 5 via 4a.

The transformation 5→6 establishes the protecting group $R^1$ which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is pre- LiCH₂CO₂R⁶; wherein R⁶ is benzyl, p-methoxybenzyl, 2,4-dimethoxybenzyl or the like; which reagent is typically generated in situ on treatment of the appropriate R⁶ acetate with a strong base such as LDA, lithium hexamethyldisilazide, lithium 2,2,6,6-tetramethylpiperide, or the like.

If desired, a more readily removable carboxyl protecting group may conveniently replace the first established group, R⁶, by the carboxyl protecting group R⁷. This transformation 12→13→14 is accomplished by selectively deblocking 12 to form 13 by hydrogenation or hydrolysis. Typically, the reaction is accomplished by treating 12 in a solvent such as methanol, ethanol, dioxane, tetrahydrofuran, water or the like under a hydrogenation pressure of from 1 to 4 atmospheres in the presence of a catalyst such as Pd on charcoal, Pd(OH)₂, or the like for from 0.1 to 10 hours. The 13 intermediate (M may be H, Na, K or ammonium such as Et₃NH, for example) need not be isolated. Intermediate 14 is obtained from the hydrogenation mixture upon treatment with the chosen reagent calculated to establish R⁷ such as an aralkyl halide in a solvent such as dimethylformamide, acetonitrile, hexamethylphosphoramide at a temperature of from 0° to 50° C. for from 0.5 to 18 hours. R⁷ is typically an aralkyl group such as p-nitrobenzyl, or o-nitrobenzyl, for example.

The oxidation 14→15 is accomplished by treating 14 in a solvent such as methylene chloride, acetonitrile, or the like with an oxidizing system such as dipyridine chromium (VI) oxide, 3,5-dimethylpyrazole chromium (VI) oxide, pyridinium chlorochromate, pyridinium dichromate, trifluoroacetic anhydride-dimethylsulfoxide, acetic anhydride-dimethyl sulfoxide or the like at a temperature of from −78° C. to 25° C. for from 5 min. to 8 hrs.

Removal of protecting groups R¹ and R²(15→16) is accomplished by acidic aqueous hydrolysis of 15 in a solvent such as methanol, ethanol, tetrahydrofuran, dioxane or the like in the presence of an acid such as hydrochloric, sulfuric, acetic or the like at a temperature of from 0° to 100° C. for from 2 to 18 hours.

The diazo species 17 is prepared from 16 by treating 16 in a solvent such as CH₃CN, CH₂Cl₂, THF or the like with an azide such as p-carboxybenzenesulfonylazide, toluenesulfonylazide, methanesulfonylazide or the like in the presence of a base such as triethylamine, pyridine, (C₂H₅)₂NH or the like for from 1 to 50 hours at 0°-25° C.

Cyclization (17→18) is accomplished by treating 17 in a solvent such as benzene, toluene, THF or the like at a temperature of from 50°-110° C. for from 1-5 hours in the presence of a catalyst such as bis (acetylacetonato)Cu (II) [Cu(acac)₂], CuSO₄, Cu powder, Rh(OAc)₂, or Pd(OAc)₂. Alternatively, the cyclization may be accomplished by irradiating 17 through a pyrex filter (a wave length greater than 300 nm) in a solvent such as benzene, CCl₄, diethylether or the like at a temperature of from 0°-25° C. for from 0.5 to 2 hours.["OAc"=acetate.]

Establishment of leaving group X (18→19) is accomplished by acylating the keto ester 18 with an acylating agent R°X such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, or the like wherein X is the corresponding leaving group such as toluene sulfonyloxy, p-nitrophenylsulfonyloxy, methanesulfonyloxy, p-bromophenylsulfonyloxy and other leaving groups which are established by conventional procedures and are well known in the art. Typically, the above acylation to establish leaving groups X is conducted in a solvent such as methylene chloride, acetonitrile or dimethylformamide, in the presence of a base such as diisopropylethylamine, triethylamine, 4-dimethylamino-pyridine or the like at a temperature of from −20° to 40° C. for from 0.5 to 5 hours. The leaving group X of intermediate 19 can also be halogen. The halogen leaving group is established by treating 18 with a halogenating agent such as φ₃PCl₂, φ₃PBr₂, (φO)₃PBr₂, oxalyl chloride or the like in a solvent such as CH₂Cl₂, CH₃CN, THF, or the like in the presence of a base such as diisopropylethylamine, triethylamine, or 4-dimethylaminopyridine or the like. [φ=phenyl.]

The reaction 19→20 is accomplished by treating 19 in a solvent such as dioxane, dimethylformamide, dimethylsulfoxide, acetonitrile, hexamethylphosphoramide, or the like in the presence of an approximately equivalent to excess of the mercaptan reagent HSCH₂CH₂NHR⁸ wherein R⁸ is hydrogen or a readily removable N-protecting group such as p-nitrobenzyloxycarbonyl, o-nitrobenzyloxycarbonyl, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent, HSCH₂CH₂NHR⁸, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step 20→I is accomplished by conventional procedures such as hydrolysis or hydrogenation. Typically 20 in a solvent such as dioxane-water-ethanol, tetrahydrofuran-aqueous dipotassium hydrogen phosphate-isopropanol or the like is treated under a hydrogen pressure of from 1 to 4 atmospheres in the presence of a hydrogenation catalyst such as palladium on charcoal, palladium hydroxide, or the like at a temperature of from 0° to 50° C. for from 0.5 to 4 hours to provide I.

In the above-discussed aldol reaction 7→8 for introduction of the hydroxyethyl side chain, the scheme proceeds directly to give a mixture of isomers (trans-R, trans-S, and cis R) from which the desired trans-R isomer can be separated chromatographically or by crystallization. An indirect aldol reaction scheme stereoselectively provides the desired trans-R isomer according to the following scheme:

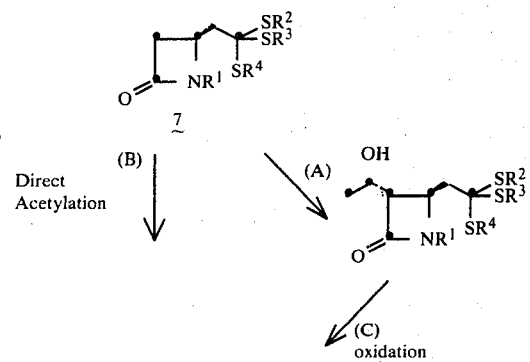

7

-continued

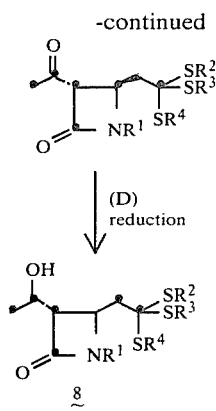

In words relative to the above reaction scheme, Step A has been described above. The direct acetylation, Step B, is accomplished by treating 7 with two or more equivalents of a base such as lithium diisopropylamide, lithium hexamethyldisilazide, lithium 2,2,6,6-tetramethylpiperidide, in a solvent such as tetrahydrofuran, diethylether, or dimethoxyethane, for example, at a temperature of from −100° to −20° C. with an acylating agent such as N-acetyl imidazole or the like. Addition of the 7 plus base mixture to the acylating agent is preferred.

The oxidation Step C is accomplished with an oxidizing agent such as dipyridine chromium(VI)oxide, trifluoroacetic anhydride-dimethylsulfoxide-triethylamine, pyridinium dichromate, acetic anhydride-dimethylsulfoxide in a solvent such as methylene chloride, acetonitrile, or the like at a temperature of from −78° to 25° C. for from 5 minutes to 5 hours.

The reduction Step D is accomplished by contacting the ketone with a reducing agent such as potassium tri(sec-butyl)borohydride, lithium tri(sec-butyl)borohydride, sodium borohydride, sodium tris(methoxyethoxy)aluminum hydride, lithium aluminum hydride or the like in a solvent such as diethylether, tetrahydrofuran, toluene or the like at a temperature of from −20° to 25° C. The reaction can conveniently be conducted in the presence of an added complexing salt such as potassium iodide, magnesium bromide or the like.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation.

EXAMPLE 1

Preparation of 4(S)-4-Iodomethylazetidin-2-one

STEP A

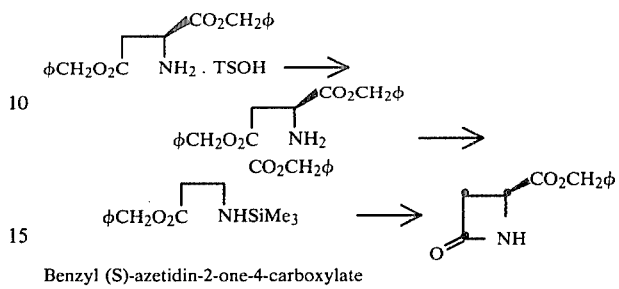

Benzyl (S)-azetidin-2-one-4-carboxylate

To a 1000 ml separatory funnel are added dibenzyl (S)-aspartate p-toluenesulfonic acid salt (48.6 g, 0.1 mole), ice-cold diethyl ether (300 ml), ice-cold water (100 ml), and ice-cold saturated aqueous potassium carbonate (50 ml). The mixture is shaken vigorously and the layers are separated. The aqueous portion is extracted with more cold diethyl ether (2×100 ml). The combined ether solution is washed with brine, dried with magnesium sulfate, and evaporated under vacuum to provide dibenzyl (S)-aspartate (31.4 g, 0.1 mole) as a colorless liquid The dibenzyl (S)-aspartate in anhydrous diethyl ether (200 ml) is cooled in an ice-bath under a nitrogen atmosphere. Trimethylchlorosilane (12.7 ml, 0.1 mole) is added to the stirred solution to give a white precipitate. Triethylamine (14.0 ml, 0.1 mole) is then added to the mixture. The cooling bath is removed and the mixture is stirred at room temperature (22°–25° C.) for 2 hrs. The mixture is then filtered directly into a 3-neck, 1.0 liter, round bottom flask fitted with a sintered glass funnel, magnetic stirrer, and a vacuum-nitrogen inlet. This operation is carried out under a blanket of nitrogen, care being taken to exclude atmospheric moisture. The sintered glass funnel is replaced by a stopper and the ether is evaporated under vacuum with stirring to provide dibenzyl (S)-N-trimethylsilylaspartate (35.5 g, 0.092 mole) as a slightly hazy oil.

Anhydrous diethyl ether (250 ml) is added to the flask containing the silyl derivative and the magnetic stirrer is replaced by a mechanical stirrer. The resulting solution is stirred under a nitrogen atmosphere with ice-bath cooling. Ethereal ethyl magnesium bromide (34 ml of a 2.94 M solution, 0.1 mole) is added dropwise over 40 min. to give a cream colored, stirable precipitate. The cooling bath is removed and the mixture is stirred at room temperature. After 1.5 hrs, a viscous gum forms. The mixture is allowed to stand overnight at room temperature. The mixture is then cooled in an ice-methanol bath while ammonium chloride saturated 2 N hydrochloric acid (100 ml) is added slowly with stirring. The resulting mixture is diluted with ethyl acetate (100 ml) and water (100 ml) and the layers are separated. The aqueous portion is extracted with more ethyl acetate (3×100 ml). The combined organic solution is washed with water (200 ml), 5% aqueous sodium bicarbonate solution (100 ml), water (100 ml), and brine, dried with magnesium sulfate, and filtered. Evaporation of the solvent under vacuum gives an orange oil interspersed with a fine, granular precipitate (25.3 g). This material is dissolved in warm chloroform (75 ml), diluted with petroleum ether (125 ml), seeded, scratched, and cooled in an ice-bath. The precipitate is collected, washed with petroleum ether, and dried under vacuum to give benzyl (S)-azetidin-2-one-4-carboxylate (3.85 g) as an off-white solid mp 136°-139° C. The mother liquors and washings are combined, diluted with petroleum ether to 500 ml, seeded, and left in a refrigerator for several days. The resulting precipitate is collected, washed with petroleum ether, and dried under vacuum to give additional product (0.82 g) as pale yellow crystals. Recrystallization of a sample from chloroform-petroleum ether gave the product as small, white flakes: mp 141°-143°; $[\alpha]_D = -43.4°$ (c3.275 in $CHCl_3$); IR($CHCl_3$) 3425, 1778, 1746 cm$^{-1}$; $^1$H NMR($CDCl_3$) δ3.00 (ddd, 1,J = 1.9, 3.2, and 14.6 Hz, H-3a), δ3.35 (ddd, 1, J = 1.5, 5.4, and 14.6 Hz, H-3b), δ4.20 (dd, 1, J = 3.2 and 5.4 Hz, H-4), δ5.22 (s, 2, $OCH_2Ph$), δ6.48 (m, 1, NH), 7.38 (s, 5, phenyl); mass spectrum m/e 205 (M+), 163, 91, 70, 43.

Anal. Calcd. for $C_{11}H_{11}NO_3$: C, 64.38; H, 5.40; N, 6.83. Found: C, 64.10; H, 5.70; N, 6.77.

STEP B

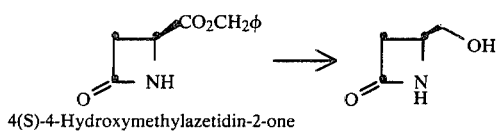

4(S)-4-Hydroxymethylazetidin-2-one

Sodium borohydride (3.69 g, 97.5 mmol) is added in one portion to a suspension of benzyl 4(S)-azetidin-2-one-4-carboxylate (20.0 g, 97.5 mmol) in 300 ml of absolute methanol at 0° C. The mixture is then allowed to warm slowly with periodic cooling being supplied to keep the internal temperature <30° C. After stirring for 2 hr., glacial acetic acid (23.4 g, 390 mmol) is added and the reaction mixture is concentrated under vacuum. The residue is treated with 500 ml of chloroform and filtered. The filtrate is concentrated under vacuum and the residue is chromatographed on 250 g of silica gel (4:1, chloroform:methanol) to yield 9.62 g (98%) of 4(S)-hydroxymethylazetidin-2-one as a white solid: m.p. 51°-53° C.; $[\alpha]_D = +68.0°$ (C=2.676 in $CHCl_3$); IR ($CHCl_3$) 3410, 1765 cm$^{-1}$ 1H NMR ($CDCl_3$) δ7.07 (1H, br. s, NH), δ4.05 (1H, br. s, OH), δ3.77 (2H, m H4, H-5a or b), δ3.58 (1H, dd, J = 11, 6, H-5a or b), δ2.97 (1H, ddd, J = 14.5, 4.8, 1.3, H3b), δ2.7 (1H, br. d, J = 14.5, H3a); mass spectrum m/e 101 (M+), 83.

STEP C

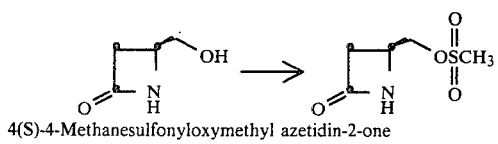

4(S)-4-Methanesulfonyloxymethyl azetidin-2-one

Methane sulfonyl chloride (11.46 g, 100 mmol) is added dropwise by syringe to a solution of 4(S)-4-hydroxymethyl azetidin-2-one (10.1 g, 100 mmol) and triethyl amine (10.1 g, 100 mmol) in 15 ml of dry methylene chloride at 0° C. (Warming is necessary in order to initially solubilize the alcohol. The resulting solution is then cooled to 0° C. prior to addition of the other reagents). The resulting solution is stirred at 0° C. for 1 hr. during which time a voluminous precipitate is produced. At the end of this time, the reaction mixture is filtered and the filtrate is concentrated under vacuum.

The two solid residues are combined and treated with 500 ml of chloroform. the resulting mixture is filtered to yield substantially pure 4(S)-4-methanesulfonyloxymethyl azetidin-2-one as a white solid. The filtrate, which contains most of the triethylamine hydrochloride, is concentrated under vacuum and chromatographed on 200 g of silica gel (4:1 chloroform:methanol) to yield an additional quantity of mesylate. This material is combined with that obtained previously and recrystallized from chloroform to yield 15.57 g (87%) of 4(S)-4-methanesulfonyloxymethylazetidin-2-one as colorless needles: m.p. 109.5°-110.5° C.; $[\alpha]_D = +25.8°$ (C = 1.025 in $H_2O$);

NMR ($D_2O$) δ4.62 (1H, dd, J = 11.2, 3.0, H-5a or b), δ4.43 (1H, dd, J = 11.2, 6, H-5a or b), δ4.12 (1H, m, H4) δ3.26 (3H, s

δ3.19 (1H, dd, J = 15, 4.5, H3b).

δ2.88 (1H, dd, J = 15, 2.5, H3a); mass spectrum m/e 179 (M+), 136;

Anal: Calc: C, 33.51; H, 5.06; N, 7.82; S, 17.89. Found: C, 33.54; H, 5.08; N, 7.72; S, 17.93.

STEP D

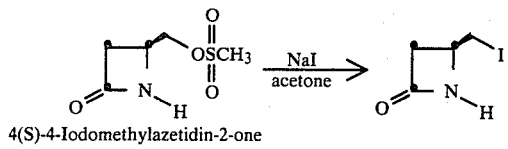

4(S)-4-Iodomethylazetidin-2-one

A mixture of 4(S)-4-methanesulfonyloxy azetidin 2-one (11.8 g, 65.9 mmol) and powdered sodium iodide (19.8 g, 132 mmol) in 130 ml of acetone is heated at reflux for 6 hr. The resulting reaction mixture is concentrated in vacuo, treated with 200 ml of chloroform and filtered. The filtrate is washed with 2×50 ml of water and dried over magnesium sulfate. The organic phase is filtered, concentrated in vacuo, and chromatographed on 250 g of silica gel (ethyl acetate) to yield 11.94 g (86%) of 4(S)-4-iodomethyl-azetidin-2-one as a white solid. This material is recrystallized from ether-petroleum ether to yield white crystals: mp 91°-92° C.; $[\alpha]_D = -23.7°$ (C=1.354 in $CHCl_3$); IR ($CHCl_3$) 3450, 1765 cm$^{-1}$, 1H NMR ($CHCl_3$) δ6.13 (brs, N-H), δ3.94 (m, 1 H, Hc), δ3.36 (m, 2H, Hd and e), δ3.16 (ddd, 1H, J = 14.9, 5.4, 2.3, Ha), δ2.72 (d, d, d, 1H, J = 14.9, 2.1, 2, Hb) mass spectrum m/e 211 (M+), 168, 142, 127, 84.

EXAMPLE 2

Preparation of (4S)-1-(t-Butyldimethylsilyl)-4-iodomethylazetidin-2-one

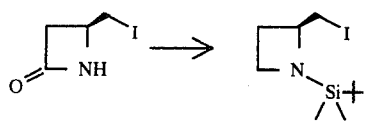

t-butyldimethylchlorosilane (7.51 g, 49.8 mmol) is added in one portion to an ice-cold, stirring solution of (4S)-4-iodomethyl-azetidin-2-one (10.0 g, 47.4 mmol) and triethylamine (5.04 g, 49.8 mmol) in anhydrous dimethylformamide (100 ml). A voluminous white precipitate forms almost immediately. The reaction mixture is stirred at 0°-5° for 1 hour and then allowed to warm to room temperature. Most of the solvent is removed under vacuum to give a residue which is partitioned between diethyl ether (250 ml) and water. The ethereal phase is washed with 2.5 N hydrochloride acid (50 ml), water (3×50 ml), and brine, dried with magnesium sulfate, filtered, and evaporated under vacuum to provide (4S)-1-(t-butyldimethylsilyl)-4-iodomethyl-azetidin-2-one (15.1 g) as a white solid. Recrystallization from petroleum ether-ethyl ether gives the product as colorless plates, mp 71°-72°; n.m.r. (CDCl₃), δ3.8 (m,1), δ2.6–3.6 (2 overlapping d of AB, 4) δ1.0 (S,9), δ0.3 (S,6), δ0.25 (S,6).

EXAMPLE 3

Preparation of (4S)-1-(t-Butyldimethylsilyl)-4-(2,2,2-tri(methylthio)-ethyl)azetidin-2-one

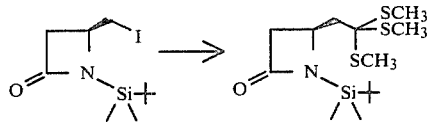

n-Butyllithium (19.4 ml of 2.5 M hexane solution, 48.5 mmol) is added slowly by syringe to a solution of tri(-methylthio)methane (7.47 g, 48.5 mmol) in 150 ml of freshly distilled THF at −78° C. The resulting solution is stirred at −78° C. for 30 min. prior to the addition of a solution of (4S)-1-(tert-butyldimethylsilyl)-4-iodomethylazetidin-2-one (15.0 g, 46.15 mmol) in 50 ml of THF. This solution is stirred at −78° C. for 30 min., then quenched by addition of saturated aqueous ammonium chloride solution. The reaction mixture is allowed to warm to room temperature, then poured into ether (250 ml), washed with water (2×100 ml) brine (100 ml) and dried over magnesium sulfate. Removal of solvents in vacuo gives an oil which is crystallized from petroleum ether to give 13.3 g (82%) of (4S)-1-(t-butyldimethylsilyl)-4-(2,2,2-tri(methylthio)ethyl)azetidin-2-one as colorless prisms. m.p. 61°-62° C. IR(CHCl₃, CM⁻¹) 2918, 2850,1730; n.m.r. (CDCl₃) δ4.0(m,1), δ3.35(dd,1,J=5.5,16), δ2,83(dd,1,J=3,16) δ2,5(ABq,2) δ2,15(s,9), δ0.98(s,9), δ0.25(s,6).

EXAMPLE 4

Preparation of (3S,4R)-1-(t-butyldimethylsilyl)-3-[(R)-1-hydroxyethyl]-4-[2,2,2-tri(methylthio)ethyl]azetidin-2-one

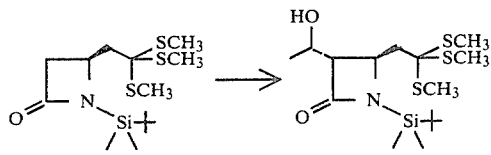

n-Butyllithium (14.8 ml of 2.5 N hexane solution, 37.0 mmol) is added by syringe to a solution of diisopropylamine (3.74 g, 37.0 mmol) in 180 ml of freshly distilled tetrahydrofuran at −78° C. The resulting solution is stirred at −78° C. for 15 min prior to the addition of a solution of (4S)-1-(t-butyldimethylsilyl)-4-[2,2,2-tri(methylthio)ethyl]azetidin-2-one (12.34 g, 35.16 mmol) in 35 ml of tetrahydrofuran. This solution is stirred at −78° C. for 10 min prior to the addition of acetaldehyde (4.62 g, 105 mmol). The solution is stirred for an additional 5 min. at −78° C. and then quenched by addition of saturated aqueous ammonium chloride solution, and allowed to warm to room temperature. The mixture is poured into 250 ml of ether and washed with water (2×100 ml) and brine and dried over magnesium sulfate. Removal of solutions in vacuo gives an oil which is chromatographed on a silica gel column (1:1 ether:petroleum ether) to give (3S,4R)-1-(t-butyldimethylsilyl)-3-[(R)-1-hydroxyethyl]-4-[2,2,2-tri(methylthio)ethyl]azetidin-2-one (7.0 g, 50.4%) at R_f=0.2. The product can be recrystallized from petroleum ether. Alternatively, the trans R product can be isolated from the crude reaction mixture by direct crystallization from a petroleum ether solution.

EXAMPLE 5

Preparation of (3S,4R)-1-(t-Butyldimethylsilyl)-3-(1-oxoethyl)-4-[2,2,2,-tri(methylthio)ethyl]azetidin-2-one

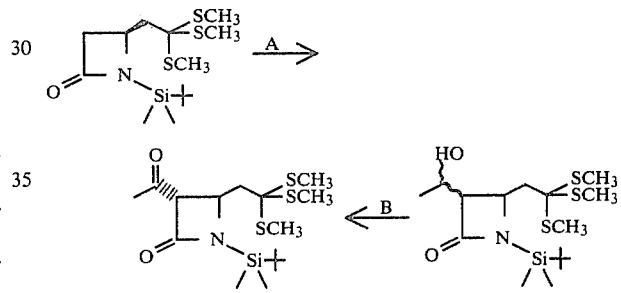

A. n-Butyllithium (2.43 ml of 2.4 m solution, 5.84 mmol) is added by syringe to a solution of diisopropylamine (591 mg, 5.84 mmol) in 25 ml of freshly distilled tetrahydrofuran at −78° C. The resulting solution is stirred at −78° C. for 15 minutes prior to the addition of a solution of (4R)-1-(t-butyldimethylsilyl)-4-[2,2,2-tri(-methylthio)ethyl]azetidin-2-one (1.00 g, 2,85 mmol) in tetrahydrofuran (5 ml). This solution is stirred at −78° C. for 15 minutes, then added via a Teflon tube to a mixture of N-acetylimidazole (642 mg, 5.84 mmol) in 25 ml of THF at −78° C. The resulting yellow reaction mixture is stirred at −78° C. for 10 minutes, then quenched by addition of saturated aqueous ammonium chloride solution. The mixture is diluted with ether (200 ml) and washed with 2.5 N hydrochloric acid solution (50 ml), water (50 ml) and brine (50 ml) and dried over magnesium sulfate. Removal of solvents in vacuo gives a yellow oil which is chromatographed on silica gel (30% ether in petroleum ether) to yield (3S,4R)-1-(t-butyldimethylsilyl)-3-(1-oxoethyl)-4-[2,2,2-tri(methyl-thio)ethyl]azetidin-2-one. n.m.r. (CDCl₃) δ4.42(m,1), δ4.32(d,1) δ2.35(m,2), δ2.32(s,3), δ2.2(s,9), δ0.98(s,9), δ0.3(2s,6).

B. Trifluoroacetic anhydride (400 mg., 1.905 mmol) is added by syringe to a solution of dimethyl sulfoxide (2.53 mmol) in dry methylene chloride (5 ml) at −78° C. The resulting mixture is stirred at −78° C. for 30 minutes prior to the addition of a solution of (3RS,4R)-1-(t-butyldlimethylsilyl)-3-[(RS)-1-hydroxyethyl]-4-[2,2,2-tri(methylthio)ethyl]azetidin-2-one (500 mg., 1.27 mmol) in dry CH₂cl₂ (1 ml). The resulting solution is stirred for 30 minutes prior to the addition of triethylamine (360 mg., 3.56 mmol). The cooling bath is removed. After 40 minutes, the reaction mixture is diluted with CH₂Cl₂, washed with water and brine and dried over magnesium sulfate. Removal of solvents in vacuo gives an oil which is purified as above. Yields 432 mg. (86%).

EXAMPLE 6

Preparation of (3S,4R)-1-(t-butyldimethylsilyl)-3-[(R)-1-hydroxyethyl]-4-[2,2,2-tri(methylthio)ethyl]azetidin-2-one

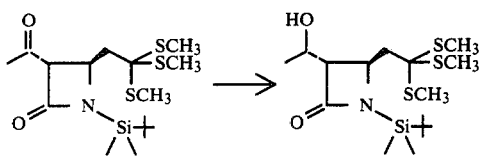

K-Selectride® (3.64 ml of 0.5 M, 1.82 mmol) is added by syringe to a mixture of potassium iodide (126 mg.,0.758 mmol) and (3S,4R)-1-(t-butyl dimethylsilyl)-3-(1-oxoethyl)-4-[2,2,2-tri(methylthio)ethyl]azetidin-2-one (298 mg, 0758 mmol) in freshly distilled ethyl ether (8 ml) at room temperature. The resulting mixture is stirred at room temperature for 2.5 hours, then quenched by the addition of acetic acid (218 mg., 3.64 mmol). The resulting mixture is diluted with ethyl acetate (25 ml) and filtered through celite. Removal of solvents in vacuo gives an oil which is chromatographed on silica gel (ether:petroleum ether) to yield 252 mg of (3S,4R)-1-(t-butyldimethylsilyl)-3-[(R)-1-hydroxyethyl]-4-[2,2,2-tri(methylthio)ethyl]azetidin-2-one. N.M.R. (R isomer, CDCl₃+D₂O) δ4.15(dq,1), δ3.95(ddd,1,J=9.5,2.3), δ3.26(dd,1,J=8,2.3), δ2.37(m,2), δ2.16(s,9), δ1.37(d,3,J=6,6), δ1.0(s,9), δ0.26(s,6).

EXAMPLE 7

Preparation of (3S,4R)-1-(t-Butyldimethylsilyl)-3-((R)-1-hydroxyethyl)-4-carbomethoxymethylazetidin-2-one

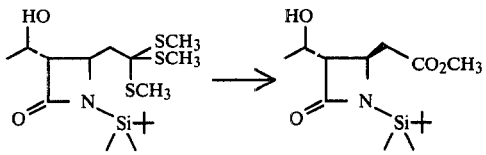

Mercuric chloride (12.37 g, 45.6 mmol) is added in one portion to a solution of (3S,4R)-1-(t-butyldimethylsilyl)-3-[(R)-1-hydroxyethyl]-4-[2,2,2-tri(methylthio)ethyl]azetidin-2-one (6.0 g, 15.2 mmol) in 250 ml of absolute methanol at 0° C. The resulting mixture (heavy white precipitate) is stirred at 0° C. for 3 min., then quenched by addition of sodium bicarbonate (8.99 g,107 mmol). This mixture is then filtered and the solid residue is washed with additional methanol. The combined filtrate and washings are concentrated in vacuo and the residue is partitioned between ethyl acetate and saturated aqueous ammonium chloride solution. The organic phase is separated, washed with saturated aqueous ammonium chloride solution, water and brine and dried over magnesium sulfate. Removal of solvents in vacuo gives an oil which is chromatographed on a silica gel column (3:2 cyclohexane:ethyl acetate) to yield (3S,4R)-1-(t-butyldimethylsilyl)-3-[(R)-1-hydroxyethyl)]-4-carbomethoxymethyl azetidin-2-one.

EXAMPLE 8

Preparation of (3S,4R)-1-(t-Butyldimethylsilyl)-3-[(R)-1-(t-butyldimethylsilyloxy)ethyl]-4-carbomethoxymethylazetidin-2-one

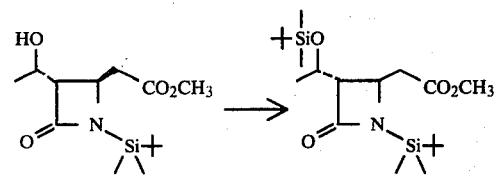

t-Butyldimethylchlorosilane (940 mg, 6.25 mmol) is added in one portion to a solution of (3S,4R)-1-(t-butyldimethylsilyl)-3-[(R)-1-hydroxyethyl]-4-carbomethoxymethylazetidin-2-one (1.88 g, 6.25 mmol) and triethylamine (1.27 g, 6.25 mmol) in 15 ml of anhydrous diemthylformamide at 0° C. After 15 min. at 0° C. the cooling bath is removed and the reaction mixture is stirred at room temperature for 24 hrs. Ether (100 ml) is added and the mixture is filtered, then washed with 2.5 N hydrochloric acid (20 ml), water (3×20 ml) and brine. The organic phase is dried over magnesium sulfate, then concentrated in vacuo. The residue is chromatographed on silica gel (7:3 petroleum ether:ether) to yield (3S,4R)-1-(t-butyldimethylsilyl)-3-[(R)-1-(t-butyldimethylsilyloxy)ethyl]-4-carbomethoxymethylazetidin-2-one. n.m.r. (CDCl₃) δ4.1(m,2), δ3.68(S,3), δ3.03(dd,1,J=4.3,2.7), δ2.8(ABq,2), δ1.17(d,3,J=6.6), δ0.98(s,9), δ0.89(s,9), δ0.23(s,6), δ0.1(s,6).

EXAMPLE 9

Preparation of (3S,4R)-1-(t-Butyldimethylsilyl)-3-[(R)-1-(t-butyldimethylsilyloxy)ethyl]-4-(2-oxoethyl)azetidin-2-one

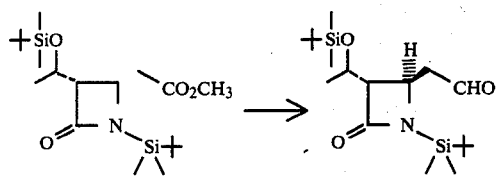

Diisobutylaluminum hydride (3.72 ml of 0.91 M in hexane, 3.38 mmol) is added slowly by syringe to a solution of (3S,4R)-1-(t-butyldimethylsilyl)-3-[(R)-1-(t-butyldimethylsilyloxy)ethyl]-4-carbomethoxymethyl azetidin-2-one (936 mg, 2.26 mmol) in 25 ml of freshly distilled toluene at −78° C. The resulting solution is stirred at −78° C. for 3 hrs., then quenched by addition of 2.5 N hydrochloric acid (5 ml). The resulting mixture is stirred for 2 min., then poured into a separatory funnel containing 100 ml of ether and 50 ml of 1.25 N hydrochloric acid saturated with tartaric acid. The organic phase is separated and the aqueous phase is extracted with ether (2×50 ml). The combined organic phases are washed with brine and dried over magnesium sulfate. Removal of solvents in vacuo gives a white solid which is recrystallized from ether-petroleum ether to give (3S,4R)-1-(t-butyldimethylsilyl)-3-[(R)-1-(t-butyldimethylsilyloxy)ethyl]-4-(2-oxoethyl)-azetidin-2-one. m.p. 115°–116° C.; n.m.r. (CDCl₃) δ4.1(m,1), δ4.03(m,1), δ2.7–3.2(m,3), δ1.23(d,3,J=6.4), δ1.08(s,9), δ0.9(s,9), δ0.25(s,6), δ0.1(s,6), δ9.83(t, 1, J=1.4).

EXAMPLE 10

Preparation of (3S,4R)-1-(t-Butyldimethylsilyl)-3-[(R)-1-(t-butyldimethylsilyloxy)ethyl]-4-(3-benzyloxycarbonyl-2-hydroxypropyl)azetidin-2-one

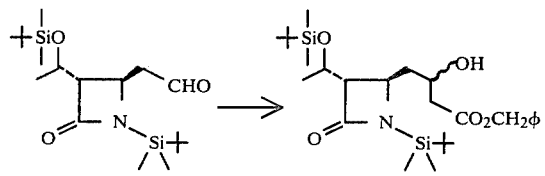

n-Butyllithium (1.81 mmol) is added by syringe to a solution of diisopropylamine (1.81 mmol) in 9 ml of freshly distilled tetrahydrofuran at −78° C. The resulting solution is stirred for 15 min at −78° C. Benzyl acetate (1.81 mmol) is then added dropwise by syringe and the resulting solution is stirred at −78° C. for 20 min. A solution of (3S,4R)-1-(t-butyldimethylsilyl)-3-[(R)-1-(t-butyldimethylsilyloxy)ethyl]-4-(2-oxoethyl)azetidin-2-one (1.64 mmol) in 3 ml of anhydrous tetrahydrofuran is added slowly by syringe. The reaction mixture is stirred at −78° C. an additional 15 min and then quenched by addition of saturated aqueous ammonium chloride solution. Ethyl acetate (50 ml) is added and the organic phase is separated, washed with water (2×10 ml) and brine and dried over magnesium sulfate. Removal of solvents in vacuo gives a white solid which is chromatographed on a short silica gel column (40% ether in petroleum ether) to yield (3S,4R)-1-(t-butyldimethylsilyl)-3-[(R)-1-(t-butyldimethylsilyloxy)ethyl]-4-(3-benzyloxycarbonyl-2-hydroxypropyl)azetidin-2-one. n.m.r. (CDCl₃) δ7.32(s,5), δ5,1(s,2), δ4.0(m,3), δ2,4-3,8(m,4), δ2.0(m,2), δ1.25(overlapping d, 3), δ0.95(s,9), δ0.9(s,9), δ0.3(s,6), δ0.18(s,6).

EXAMPLE 11

Preparation of (3S,4R)-1-(t-Butyldimethylsilyl)-3-[(R)-1-(t-butyldimethylsilyloxy)ethyl]-4-[3-(4-nitrobenzyl)oxycarbonyl-2-hydroxypropyl]azetidin-2-one

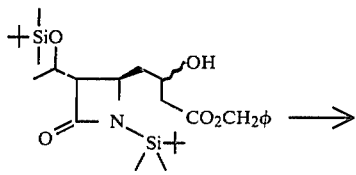

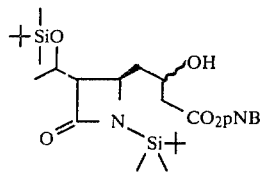

A mixture of (3S,4R)-1-(t-butyldimethylsilyl)-3-[(R)-1-(t-butyldimethylsilyloxy)ethyl]-4-(3-benzyloxycarbonyl-2-hydroxypropyl)azetidin-2-one (1.00 mmol), sodium bicarbonate (1.00 mmol) and 10% Pd/C in 20 ml of 4:1 tetrahydrofuran-H₂O is hydrogenated at 40 psi on a Parr shaker for 30 min. The mixture is then filtered through Celite and the catalyst is washed with 10 ml of water. The combined washings and filtrate are concentrated i.v. to 2 ml and lyophilized. The resulting fluffy white solid is dissolved in 5 ml of anhydrous dimethylformamide and p-nitrobenzyl bromide (216 mg, 1.00 mml) is added in one portion. The resulting solution is stirred at room temperature for 3 hrs, then diluted with ether (50 ml) and washed with water (3×10 ml) and brine and dried over magnesium sulfate. The solvents are removed in vacuo and the residue is chromatographed on silica gel to yield (3S,4R)-1-(t-butyldimethylsilyl) 3[(R)-1-(t-butyldimethylsilyloxy)ethyl]-4-[3-(4-nitrobenzyl)oxycarbonyl-2-hydroxypropyl]-azetidin-2-one. n.m.r. (CDCl₃) δ7.85(2d-aromatic,4), δ5,26(s,2), δ4.2(m,3), δ2,5-3.6(m,4) δ2.0(m,2), δ1.4(2 overlapping d,3), δ1.0(2s,18), δ0.25(2s,12).

EXAMPLE 12

Preparation of (3S,4R)-1-(t-Butyldimethylsilyl)-3-[(R)-1-(t-butyldimethylsilyloxy)ethyl]-4-[3-(4-nitrobenzyl)oxycarbonyl-2-oxopropyl]azetidin-2-one

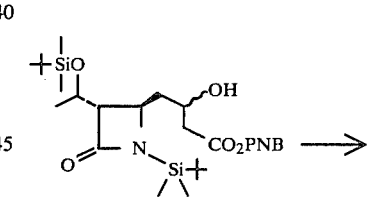

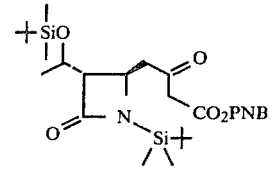

Anhydrous chromium trioxide (10.0 mmol) is added to a soution of anhydrous pyridine (20.0 mmol) in 30 ml of anhydrous methylene chloride. After stirring at room temperature for 15 min., the reaction mixture is treated all at once with a solution of (3S,4R)-1-(t-butyldimethylsilyl)-3-[(R)-1-(t-butyldimethylsilyloxy)ethyl]-4-[3-(4-nitrobenzyl)oxycarbonyl-2-hydroxypropyl]-azetidin-2-one (1.00 mmol) in anhydrous methylene chloride (8 ml). The resulting mixture is stirred at room temperature for 5 min. The CH₂Cl₂ layer is decanted from the dark, tarry residue which is triturated with more CH₂Cl₂. The combined CH₂Cl₂ phase is concentrated in vacuo. The residue is triturated with ether (100 ml) and the ether extracts are filtered. The filtrate is washed with 5% aqueous sodium bicarbonate solution, 2.5 N HCl, 5% NaHCO₃ and brine, dried over magnesium sulfate and concentrated in vacuo to yield (3S,4R)-1-(t-butyldimethylsilyl)-3-[(R)-1-(t-butyldimethylsilyloxy)ethyl]-4-[3-(4-nitrobenzyl)oxycarbonyl-2-oxopropyl]azetidin-2-one. n.m.r. (CDCl₃) δ7.85(2d-aromatic, 4), δ5.27(s,2), δ4.05(m,2), δ3.6(s,2), δ2.4–3.2(dd overlapping ABq,3), δ1.2(d,3,J=6.6), δ0.9(2s,18), δ0.22(s,6), δ0.05(s,6).

EXAMPLE 13

Preparation of (3S,4R)-3-[(R)1-hydroxyethyl]-4-[3-(4-nitrobenzyl)oxycarbonyl-2-oxopropyl]azetidin-2-one

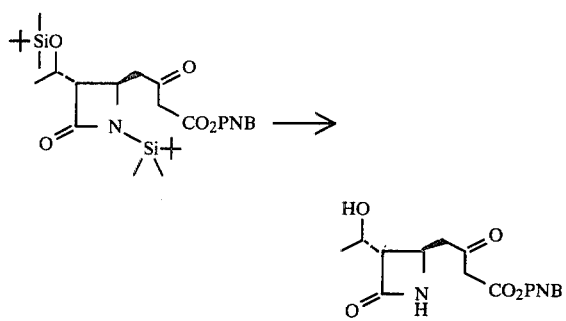

(3S,4R)-1-(t-butyldimethylsilyl)3-[(R)-1-(t-butyldimethylsilyloxy)ethyl]-4-[3-(4-nitrobenzyl)oxycarbonyl-2-oxopropyl]azetidin-2-one (7.9 mmol) is dissolved in 160 ml of 9:1 (v/v) methanol-water and cooled to 0° C. Concentrated hydrochloric acid (2.75 ml) is added and the resulting solution is stirred at 0° C. for 15 min., then allowed to warm to room temperature. The solution is stirred at room temperature for 2.5 hrs, then diluted with ethyl acetate (200 ml) and washed with water, saturated aqueous sodium bicarbonate solution and brine, dried over magnesium sulfate and concentrated in vacuo to yield (3S,4R)-3-[(R)1-hydroxyethyl]-4-[3-(4-nitrobenzyl)oxycarbonyl-2-oxopropyl]-azetidin-2-one.

EXAMPLE 14

Preparation of (3S,4R)-3-[(R)-1-hydroxyethyl]-4-[3-(4-nitrobenzyl)oxycarbonyl-2-oxo-3-diazoproyl]-azetidin-2-one

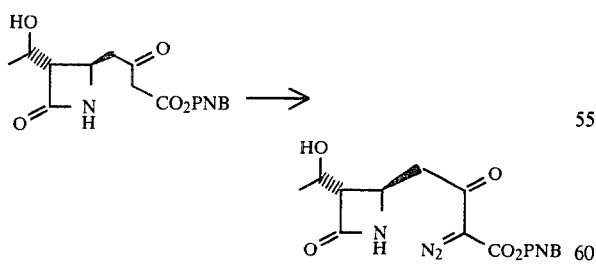

Triethylamine (263 mg, 2.6 mmol) is added by syringe to a mixture of (3S,4R)-3-[(R)-1-hydroxyethyl]-4-[3-(4-nitrobenzyl)oxycarbonyl-2-oxopropyl]azetidin-2-one (253 mg, 0.72 mmol) and p-carboxybenzene sulfonylazide (196 mg, 0.84 mmol) in dry acetonitrile (6 ml) at 0° C. When addition is complete the cooling bath is removed and the reaction mixture is stirred at room temperature for 1 hour. The mixture is then diluted with ethyl acetate (50 ml) and filtered. The filtrate is concentrated in vacuo and the residue is chromatographed on a short silica gel column (ethyl acetate) to yield 222 mg, (81% overall from (3S,4R)-1-(t-butyldimethylsilyl)-3-[(R)-1-(t-butyl dimethylsilyloxy)ethyl]-4-[3-(4-nitrobenzyl)oxycarbonyl-2-oxopropyl]azetidin-2-one) of (3S,4R)-3-(R)-1-hydroxyethyl)-4-[3-(4-nitrobenzyl)oxycarbonyl-2-oxo-3-diazopropyl]azetidin-2-one as a white solid m.p. (dec.) 163° C. IR(CHCl₃, CM⁻¹) 3410, 2132, 1756, 1718, 1650, 1350, 1280, 1120; n.m.r. (CDCl₃)δ7.9(2d-aromatic,4),δ5.4(s,2), δ6.2(brs,1),δ4.1(m,2),δ2.6–3.6(m,4),δ1.32(d,3,J=6.2).

EXAMPLE 15

Preparation of (5R,6S)p-Nitrobenzyl 6-[(R)1-hydroxyethyl]-1-azabicyclo[3.2.0]heptan-3,7-dione-2-carboxylate

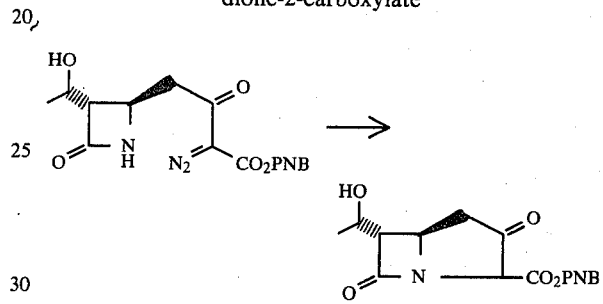

A suspension of (3S,4R)-3-[(R)-1-hydroxyethyl]-4-[3-(4-nitrobenzyl)oxycarbonyl-2-oxo-3-diazopropyl]azetidin-2-one (56.4 mg, 0.15 mmol) and rhodium (II) acetate (0.1 mg) in dry benzene (3 ml) is deoxygenated by bubbling through nitrogen for 10 minutes. The mixture is then heated to 78° C. for 1 hour. During heating the solid starting material gradually goes into solution. The mixture is then cooled, filtered to remove the catalyst, and the filtrate is concentrated in vacuo to yield (5R,6S) p-nitrobenzyl 6-[(R)-1-hydroxyethyl]-1-azabicyclo[3.2.0]heptan-3,7-dione-2-carboxylate, 51 mg. (98%) as a colorless oil which slowly crystallized at room temperature (22° C.).

Physical Properties:

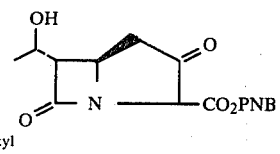

PNB = p-nitrobenzyl n.m.r.: (300 MHz, CDCl₃)δ8.26, 7.54 (aromatic, 4), 5.29 (AB,2), 4.77 (s,1), 4,32(dg,1,J=6.6,7), 4.16(ddd,1, J=7,7.5,2.2), 3.21(dd,1,J=7,2.2), 2.94(dd,1,J=19.5,7) 2.50(dd,1,J=19.5,7.5), 2.2(brs,1), 1.37(d,3,J=6.6).
I.R.: (CHCl₃,CM⁻¹) 1770, 1758, 1610, 1522, 1353. m.p. 110°–111° C.

EXAMPLE 16

Preparation of p-Nitrobenzyloxycarbonylaminoethanethiol

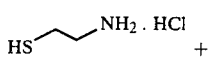

+

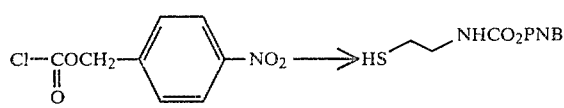

To 600 ml diethyl ether (Et$_2$O)—75 ml H$_2$O in an ice bath with stirring is added 3.2 g cysteamine hydrochloride (mw=114; 28.1 mmole). A solution of 7.14 g NaHCO$_3$ (mw=84; 85 mmole) in 75 ml H$_2$O is added. The ice bath is removed, and at room temperature a solution of 6.75 g p-nitrobenzylchloroformate (mw=216; 31.3 mmole) in 270 ml Et$_2$O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et$_2$O. The combined Et$_2$O layers are dried over anhydrous MgSO$_4$, filtered, and concentrated under a N$_2$ stream. The crystalline residue is slurried in a small amount of ether, filtered, and the pale yellow crystals are dried under high vacuum to give 4.7 g. p-nitrobenzyloxycarbonylaminoethanethiol (65% yield). NMR (CDCl$_3$): 8.18 (d, J=8 Hz, aromatic protons ortho to nitro), 7.47 (d, J=8 Hz, aromatic protons meta to nitro), 5.27 (—NH—), 5.20 (s, CH$_2$—NH—), 2.67 (m, —CH$_2$—SH), 1.35 (t, J=8.5 Hz, —SH) in ppm downfield from TMS. IR (CHCl$_3$ solution): carbonyl-1725 cm$^{-1}$. M.S.: molecular ion-256, (M-47) at 209, (M-136) at 120, +CH$_2\phi$pNO$_2$ at 136.

EXAMPLE 17

Preparation of (5R,6S) p-Nitrobenzyl 3[2-(p-nitrobenzyloxycarbonyl)amino ethylthio]-6-[(R)-1-hydroxyethyl)-1-azabicyclo [3,2,0]-hept-2-en-7-one-2-carboxylate

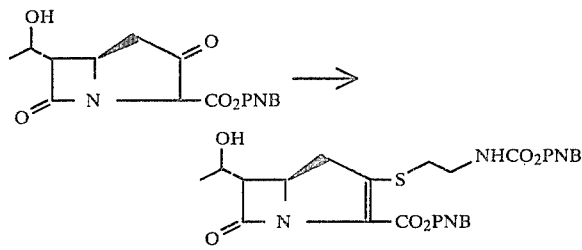

(5R,5S) p-Nitrobenzyl 6-[(R)1-hydroxyethyl]-1-azabicyclo [3,2,0]heptan-3,7-dione-2-carboxylate(51 mg, 0.147 mmol) is dissolved in acetonitrile (3 ml) and the resulting solution is cooled to 0° C. Diisopropylethylamine (22 mg, 0.17 mmol) is added by syringe and the resulting solution is stirred at 0° C. for 1 minute prior to the addition of a solution of freshly recrystallized p-toluene sulfonic anhydride (51 mg., 0.156 mmol) in dry acetonitrile (1 ml). The resulting solution is stirred at 0° C. for 1 hour to provide (5R,6S)p-nitrobenzyl 3-(p-toluenesulfonyloxy)-6-[(R)-1-hydroxyethyl]-1-azabicyclo[3.2.0]-hept-2-en-7-one-2-carboxylate, then cooled to −25° C. Diisopropylethylamine (80.5 mg, 0.624 mmol) is added by syringe followed shortly thereafter by a solution of N-p-nitrobenzyloxycarbonylcysteamine (40 mg, 0.156 mmol) in 1 ml of dry acetonitrile. The reaction mixture is then stored in a refrigerator for 70 hr. The mixture is diluted with 25 ml of ethyl acetate washed with brine and dried over magnesium sulfate. Solvents are removed in vacuo to yield a yellow oil which is chromatographed on a silica gel plate (ethyl acetate, R$_f$=0.4) to yield (5R,6S) p-nitrobenzyl-3-[2-(p-nitrobenzyloxycarbonyl)amino ethylthio]-6-[(R)-1-hydroxyethyl]-1-azabicyclo [3,2,0]-hept-2-en-7-dione-2-carboxylate as a yellow solid, m.p. 167°–169° C. IR(-Nujol mull) 1773 and 1690 cm$^{-1}$; n.m.r. (CDCl$_3$)δ7.54–8.26(overlapping ABq,4),δ5.40(ABq,2), δ5.22(s,2),δ4.27(m,2),δ3.47 (m),δ3.23(dd,1),δ3.14(dd,1)δ3.40(dd,1),δ3.04(m,2), δ1.37(d,3).

EXAMPLE 18

Preparation of Thienamycin

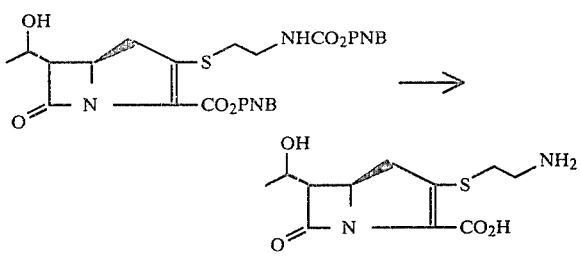

A mixture of N-p-nitrobenzyloxycarbonyl thienamycin p-nitrobenzyl ester (10 mg, 0.017 mmol) and 10% Pd/C-Bolhofer type in tetrahydrofuran (2 ml), 0.1 M dipotassium hydrogen phosphate solution (1.4 ml) and 2-propanol (0.2 ml) is hydrogenated at 40 psi on the Parr shaker for 30 minutes. The mixture is then filtered and the catalyst is washed with water (3×3 ml). The combined filtrate and washings are extracted with ethyl acetate-ethyl ether then concentrated to ~3 ml and lyophilized. The resulting white powder is identical to natural thienamycin in all respects.

EXAMPLE 19

Preparation of Benzyl (4-S)-azetidin-2-one-4-carboxylate

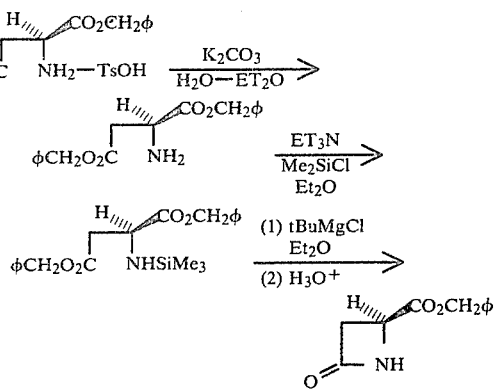

A mixture of dibenzyl (S)-aspartate p-toluene-sulfonic acid salt (48.6 g, 0.1 mole) diethylether (300 ml), water (100 ml), and saturated aqueous potassium carbonate (50 ml) is shaken vigorously. The layers are separated and the aqueous portion is extracted with more ether (2×100 ml). The combined ethereal extracts are washed with brine, dried with magnesium sulfate, filtered, and evaporated under vacuum to afford dibenzyl (S)-aspartate (31.5 g) as a water white liquid.

The dibenzyl (S)-aspartate in anhydrous diethyl ether (200 ml) is cooled in an ice bath and stirred under a nitrogen atmosphere while trimethylchlorosilane (12.7 ml, 0.1 mole) and triethylamine (14.0 ml, 0.1 mole) are added successively over a few minutes. The cooling bath is removed and the mixture is stirred at room temperature for 2 hours. The mixture is then filtered under a blanket of nitrogen into a three-neck, one-liter, round bottom flask fitted with a sintered glass funnel, vacuum-nitrogen inlet, and a mechanical stirrer. Additional anhydrous ether (2×50 ml) is used to wash the precipitate of triethylammonium hydrochloride. The funnel containing the precipitate is replaced by a dropping funnel and the etheral filtrate of dibenzyl (4S)-N-trimethyl silyl-aspartate is cooled in an ice bath and stirred under a nitrogen atmosphere with 2.1 M t-butyl magnesium chloride in ether (48 ml, 0.1 mole) is added drop wise over 9 minutes. A gummy precipitate forms during the addition. The cooling bath is then removed and the mixture is allowed to stand at room temperature overnight.

The mixture is cooled in an ice-bath and stirred vigorously while ammonium chloride saturated 2 N hydrochloric acid (100 ml) is added over a few minutes. After stirring vigorously several more minutes, the mixture is diluted with water (100 ml) and ethyl acetate (100 ml) and layers are separated. The aqueous portion is extracted with ethyl acetate (2×100 ml). The combined organic solution is washed with water (100 ml), 5% aqueous sodium bicarbonate (100 ml), and brine (100 ml), dried with magnesium sulfate, filtered, and evaporated under vacuum to a yellow semi-solid. Crystallization of this material from methylene chloride (100 ml)-petroleum ether (300 ml) provides the azetidinone product (8.2 g) as an off-white powder. The mother liquors are evaporated and the residue crystallized from diethyl ether to afford additional product (2.5 g) as a pale yellow product. The two crops are combined and recrystallized from methylene chloride to yield benzyl (4S)-azetidin-2-one-4-carboxylate (9.5 g) as nearly colorless crystals: mp 139°–141°; $[\alpha]_D = -40.5°$ (C2.0 in CHCl$_3$); IR(CHCl$_3$) 3425; 1778, 1746 cm$^{-1}$; $^1$H NMR (CDCl$_3$) δ3.00 (ddd, H-3β), 3.35(ddd,H-3α), 4.20(dd,H-4), 5.22(s,CH$_2$φ), 6.48(m,NH), 7.35(s,phenyl); mass spectrum m/e 205(M$^+$), 163, 91, 70, 43.

What is claimed is:
1. The compound:

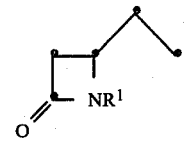

wherein R$^1$ is a protecting group selected from t-butyldimethylsilyl, t-butyldiphenylsilyl, triphenylsilyl, isopropyldimethylsilyl, and 3,4-dimethoxybenzyl.

* * * * *